United States Patent [19]

Gebauer et al.

[11] 4,385,185

[45] May 24, 1983

[54] β-γ-UNSATURATED KETONES AND ISOPRENOID 2,6 DIONES, A PROCESS FOR PRODUCING THE SAME AND THEIR USE AS FRAGRANT AND FLAVORING SUBSTANCES

[75] Inventors: Helmut Gebauer, Munich; Walter Hafner, Furth, both of Fed. Rep. of Germany

[73] Assignee: Consortium fur Elektrochemische Industrie GmbH, Fed. Rep. of Germany

[21] Appl. No.: 245,574

[22] Filed: Mar. 20, 1981

[30] Foreign Application Priority Data

Apr. 9, 1980 [DE] Fed. Rep. of Germany ....... 3013565

[51] Int. Cl.$^3$ .................... C07C 49/21; C07C 49/217; C07C 49/203
[52] U.S. Cl. .................................. 568/308; 568/376; 568/380; 568/347; 568/335; 568/659; 568/348; 568/660; 568/661; 568/391; 568/662; 568/663; 568/392; 568/626; 568/669; 568/393; 568/673; 568/579; 568/394; 568/674; 568/675; 568/821; 568/313; 568/315; 568/822; 568/316; 568/390; 568/838; 568/839; 568/841; 568/843; 568/875; 568/849; 568/715; 568/686; 568/683; 568/684; 568/685; 568/687; 252/522 R; 426/656; 568/329; 568/330; 568/331; 568/325; 568/336; 568/375; 568/379; 568/381; 568/415; 568/417
[58] Field of Search ............... 568/308, 325, 417, 329, 568/330, 331, 375, 376, 379, 381, 335, 415, 380, 336, 359, 660, 661, 662, 663, 626, 669, 673, 674, 675, 579, 821, 822, 838, 839, 841, 843, 849, 875, 715, 686, 683, 684, 685, 687

[56] References Cited

U.S. PATENT DOCUMENTS

| | | | |
|---|---|---|---|
| 3,076,847 | 2/1963 | Prelog | 568/417 |
| 3,551,463 | 12/1970 | Cywinski | 568/417 |
| 3,814,767 | 6/1974 | Ward | 568/376 |
| 3,910,897 | 10/1975 | Chodneker et al. | 568/414 |
| 4,010,207 | 0/0000 | Braunsten et al. | 568/381 |
| 4,216,172 | 8/1980 | Heine et al. | 568/381 |

FOREIGN PATENT DOCUMENTS 1244784 of 0000 Fed. Rep. of Germany .
459982 9/1968 Switzerland ........................ 568/417

OTHER PUBLICATIONS

Conia et al., Bull. Soc. Chim. Fran., pp. 273-277 (1966).
Kiese et al., Yugaku, vol. 26, p. 474 (1977).

Primary Examiner—James H. Reamer
Attorney, Agent, or Firm—Allison C. Collard; Thomas M. Galgano

[57] ABSTRACT

Compounds of the general formula I:

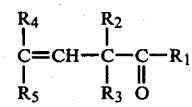

wherein $R_1$ and $R_2$ are equal or different alkyl-, alkoxyalkyl-, or aryl groups, or together form a ring; $R_3$ is an allyl or benzyl radical; and $R_4$ and $R_5$ represent hydrogen, alkyl, alkoxyalkyl, alkenyl or further compounds of the formula II:

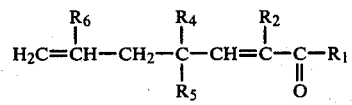

wherein $R_1$, $R_2$, $R_4$ and $R_5$ have the meaning indicated above and $R_6$ stands for hydrogen or methyl or to compounds which are modified by the addition of hydrogen to at least one olefinic or carbonylic double bond of compounds of the general formula I or II. The invention also relates to a process for preparing the new compounds. The compounds of the general formula II are obtained by thermal treatment of a selection of compounds of formula I, for which $R_3$ stands for the allyl or methallyl radical. The compounds according to the invention are used as fragrant and flavoring substances.

10 Claims, No Drawings

β-γ-UNSATURATED KETONES AND ISOPRENOID 2,6 DIONES, A PROCESS FOR PRODUCING THE SAME AND THEIR USE AS FRAGRANT AND FLAVORING SUBSTANCES

The invention relates to a new α-tertiary, β-γ-olefinic unsaturated ketones and isoprenoid 2,6-diones modified derivatives thereof obtained, respectively, by addition of hydrogen to at least one olefinic or carbonylic double bond. The invention further relates to a process for preparing these compounds, as well as their use as fragrant and flavoring substances.

German Pat. No. 12 44 784 describes a process for making ketones alkylated in α-position, which may be used as fragrances; according to that process, ketones are alkylated in α-position with organic halides in the presence of alkali hydroxide and catalytic amounts of a nitrogen base. The reactive center of the ketone is hydrogen in α-position. However, these processes yield, in general, mixtures of substances, since ketones mostly contain several hydrogen atoms in α- or α'-position.

Moreover, J. M. Conia et al, *Bull. Soc. Chim. France*, 1966 (1), pages 273–277, reports an allylating reaction of the α-substituted, α-β-unsaturated ketone 3,4-dimethyl-pent-3-en-2-one with allyl bromide in the presence of sodium-tert.-amylate in homogeneous phase, yielding 3-isopropenyl-3-methyl-hex-5-en-2-one and its further conversion to a cis-trans isomer mixture of 3,4-dimethyl-octa-4,7-dien-2-ones by thermal treatment at 230° C. However, it is a disadvantage that for the allylating reaction, equimolar amounts of sodium-tert.-amylate have to be used, the preparation of which requires the problematic reaction with metallic sodium.

Another report was published by Kiese et al in *Yugaku* 26,474 (1977) Ref. Ca 87, 133818, which describes the phase transfer catalyzed reaction of acetone and prenyl chloride to 6-methyl-hept-5-en-2-one. Alkylating reactions of ketones, which attack the hydrogen in α-position, yield only in such exceptional cases uniform products, as mentioned above, where the ketones used as starting products only have a single hydrogen in α-position.

Furthermore, the reaction of activated organic halides, such as allyl- or benzyl-halides with α-alkylated, α-β-unsaturated aldehydes has been described (see U.S. Pat. No. 4,010,207).

It has now been found that such reactions can also be carried out with α-alkylated, α-β-unsaturated ketones which are far less reactive than the aldehydes. It was to be expected that under the conditions of the phase transfer catalyzed reaction in analogy to the above-mentioned Kiese et al report that at least with a considerable loss in yield of the desired product, the hydrogen in α-position would also be alkylated. Surprisingly, however, this did not occur.

The invention thus relates to compounds of the general formula I

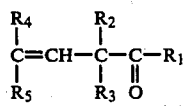

wherein:
$R_1$ and $R_2$ are the same or different alkyl, alkoxyalkyl, or aryl groups, or together form a ring;
$R_3$ is an allylic or benzylic radical; and
$R_4$ and $R_5$ represent hydrogen, alkyl, alkoxyalkyl, alkenyl or aryl.

Preferred are compounds of the above formula I, wherein:
$R_1$ represents an alkyl or alkoxyalkyl group with 1–6 carbon atoms or a phenyl group having one or, if desired, a maximum of two substituents, the substituents being optionally up to two alkyl or alkyloxy groups with 1–3 carbon atoms and/or up to 2 halogen atoms;
$R_2$ represents an alkyl or alkoxyalkyl radical with 1–5 carbon atoms or a phenyl group, having one or, if desired, a maximum of two substituents, the substituents being optionally up to two alkyl or alkyloxy groups with 1–3 carbon atoms and/or up to 2 halogen atoms;
$R_1$ and $R_2$ together may form a ring with 4–7 carbon atoms;
$R_3$ is an allylic radical with 3–5 carbon atoms, or an aromatic radical ring which, if desired, may be a benzyl radical carrying at most two further substituents, the substituents being up to two alkyl or alkoxyalkyl radicals with 1–3 carbon atoms and/or up to two halogen atoms; and
$R_4$ and $R_5$ represent hydrogen, or alkyl or alkoxyalkyl radicals with 1–6 carbon atoms, alkenyl radicals with 2–6 carbon atoms, or phenyl groups having, if desired, up to two further substituents, the substituents being optionally up to two alkyl or alkoxyalkyl groups with 1–3 carbon atoms and/or or two halogen atoms.

Especially preferred are compounds of formula I in which $R_3$ represents the allyl or methallyl radical.

The compounds have in α-position with respect to the carbonyl group a tertiary carbon atom, are olefinically unsaturated in β and γ-position and also exhibit in the γ'-δ'-position (according to $R_3$) an olefinic structural unit, which may be substituted by an aromatic structural unit. Furthermore, the β-carbon atom carries a vinyl hydrogen.

Furthermore, the invention relates to compounds of the general formula II

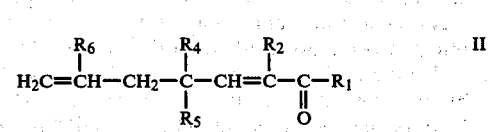

wherein:
$R_1$ and $R_2$ are the same or different alkyl, alkoxyalkyl, or aryl groups, or together form a ring;
$R_4$ and $R_5$ represent hydrogen, alkyl, alkoxyalkyl, alkenyl or aryl; and
$R_6$ is hydrogen or methyl.

Preferred are compounds of this group, wherein:
$R_1$ represents an alkyl or alkoxyalkyl group with 1–6 carbon atoms or a phenyl group having one or, if desired, at the most two substituents, the substituents optionally being up to two alkyl or alkyloxy groups with 1–3 carbon atoms and/or up to two halogen atoms;
$R_2$ represents an alkyl or alkoxyalkyl radical with 1–5 carbon atoms or a phenyl group having one or, if desired, at the most two substituents, the substituents optionally being up to two alkyl or alkyloxy groups with 1-3 carbon atoms and/or up to two halogen atoms;

or $R_1$ and $R_2$ together may form a ring with 4-7 carbon atoms;

$R_4$ and $R_5$ represent hydrogen, or alkyl or alkoxyalkyl radicals with 1-6 carbon atoms, alkenyl radicals with 2-6 carbon atoms or a phenyl group having, if desired, up to two further substituents, the substituents being optionally up to two alkyl or alkoxyalkyl groups with 1-3 carbon atoms and/or up to two halogen atoms; and $R_6$ represents hydrogen or methyl.

A further modification of the invention relates to compounds which are derived from formulas I and II by addition of hydrogen to at least one olefinic or carbonyl double bond.

A preferred process for preparing the compounds of formula I is characterized by reacting compounds of the formula

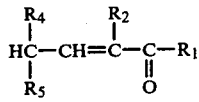

with compounds of the formula

wherein Hal stands for chloride, bromide or iodide, and wherein the reaction takes place in an organic/alkaline two-phase system in the presence of a phase-transfer catalyst.

The reaction temperatures are, in general, between 0° and 150° C., preferably between 20° and 110° C. Frequently, optimum ratios of reaction time and yield are obtained at temperatures between 60° and 70° C.

In an advantageous embodiment of the process, the two-phase system with the catalyst is first prepared and a mixture of the reaction components is added thereto drop-by-drop.

For carrying out the process, equimolar amounts of ketone and $R_3$-Hal (in the following called "alkylating agent") are required. For best yields, most of the time an excess of the alkylating agent is used, since in a side reaction, low amounts of alkylating agent are converted into the corresponding alcohol or ether.

The times for adding the reaction components drop-by-drop into the mixture vary between 10 minutes and 5 hours, depending on the reactants, amount of catalyst, and the heat of reaction. It is frequently possible to regulate the reaction temperature by adjusting the proper dropping rate.

After the addition of reactants is terminated, it may be desirable to allow an after-reaction for 1 to 5 hours in order to obtain a more complete reaction.

The work-up of the reaction mixture is done by conventional techniques. As a rule, the phases are separated and the organic phase is subjected to fractional distillation for the isolation of the desired product. The two-phase system is formed from an organic inert solvent, immiscible with water, and a 5 to 50%, preferably 20-50% aqueous solution, or alkali metal hydroxide in solid form.

Examples of inert solvents are benzene, toluene, xylene, cyclohexane, petrol ether, gasoline and the like. Mixtures may also be used. Examples of alkali metal hydroxides are NaOH, KOH and others.

Calculated on the alkylating agent used, equimolar quantities of alkali metal hydroxides are necessary. However, about a two-fold excess of the basic or alkali compound accelerates the reaction.

In accordance with the invention, phase-transfer catalysts may be used which have already been used previously in such reactions. Examples are Crown ether, quaternary ammonium and phosphonium salts, especially tetrabutyl-ammonium bromide. The catalysts are used in amounts of 0.5 to 5 mol. %, calculated on the alkylating agent, the most advantageous being, in general, 2-3 mol. %.

The ketones available as starting products are, e.g., crossed aldol condensation products of ketones containing a methylene group in α-position to the carbonyl function or group, with appropriate aldehydes.

The aldol condensation step can, if desired, be carried out together with the alkylation step in the described aqueous/alkaline two-phase system in a single pot process. This mode of operation is particularly advantageous when aldehydes having comparatively low reactivity are used as starting material (in which the formation of the unilateral aldol condensation product is not prevalent) and ketone is used in excess.

Examples of ketones to be alkylated according to the invention are aldol condensation products of methyl-ethyl-ketone; diethyl-ketone, phenyl-ethyl-ketone, methyl-propyl-ketone; dipropyl-ketone; phenyl-propyl-ketone; methyl-butyl-ketone; cyclohexanone; cyclopentanone; and acetaldehyde; propionaldehyde; butyraldehyde, isobutyraldehyde; valeraldehyde; isovaleraldehyde; 3-pentenal; 4-pentenal and others.

As alkylating agents, we may mention for instance: allyl chloride; allyl bromide; methallyl chloride, crotyl chloride; 1-chloro-1-methyl-propene-2; prenyl chloride; benzyl chloride; methoxybenzyl chloride; chlorobenzyl chloride; diphenylmethyl bromide and others.

Examples of compounds according to formula I are: 3-allyl-3-methyl-pent-4-en-2-one; 3-allyl-3-ethyl-pent-4-en-2-one; 3-allyl-3-propyl-pent-4-en-2one; 3-allyl-3-i-propyl-pent-4-en-2-one; 3-allyl-3-butyl-pent-4-en-2-one; 3-methallyl-3-methyl-pent-4-en-2-one; 3-methallyl-3-ethyl-pent-4-en-2-one; 3-methallyl-3-propyl-pent-4-en-2-one; 3-methallyl-3-i-propyl-pent-4-en-2-one; 3-methallyl-3-butyl-pent-4-en-2-one; 3-crotyl-3-methyl-pent-4-en-2-one; 3-crotyl-3-ethyl-pent-4-en-2-one; 3-allyl-3-propyl-pent-4-en-2-one; 3-crotyl-i-propyl-pent-4-en-2-one; 3-crotyl-butyl-pent-4-en-2-one; 3-benzyl-3-methyl-pent-4-en-2-one; 3-benzyl-3-ethyl-pent-4-en-2-one; 3-benzyl-3-propyl-pent-4-en-2-one; 3-benzyl-3-i-propyl-pent-4-en-2-one; 3-benzyl-3-butyl-pent-4-en-2-one; 3-p-methoxy-benzyl-3-methyl-pent-4-en-2-one; 3-p-methoxy-benzyl-3-ethyl-pent-4-en-2-one; 3-p-methoxy-benzyl-3-propyl-pent-4-en-2-one; 3-p-chlorobenzyl-3-methyl-pent-4-en-2-one; 3-p-chlorobenzyl-3-ethyl-pent-4-en-2-one; 3-m,p-dichloro-benzyl-3-methyl-pent-4-en-2-one; 3-allyl-3-methyl-hex-4-en-2-one; 3-allyl-3-ethyl-hex-4-en-2-one; 3-allyl-3-propyl-hex-4-en-2-one; 3-methallyl-3-methyl-hex-4-en-2-one; 3-methallyl-3-ethyl-hex-4-en-2-one; 3-methallyl-3-propyl-hex-4-en-2-one; 3-crotyl-3-methyl-hex-4-en-2-one; 3-crotyl-3-ethyl-hex-4-en-2-one; 3-crotyl-3-propyl-hex-4-en-2-one; 3-benzyl-3-methyl-hex-4-en-2-one; 3-benzyl-3-ethyl-hex-4-en-2-one; 3-benzyl-3-propyl-hex-4-en-2-one; 3-p-methyl-benzyl-3-methyl-hex-4-en-2-one; 3-p-methyl-benzyl-3-ethyl-hex-4-en-2-one; 3-p-methyl-benzyl-propyl-hex-4-en-2-one; 5-methyl-3-allyl-3-methyl-hex-4-en-2-one; 3-allyl-3-methyl-hept-4-en-2-one; 3-allyl-3-methyl-octa-4- en-2-one; 3-allyl-3-methyl-nona-4-en-2-one; 3-allyl-3-methyl-deca-4-en-2-one; 4-allyl-4-methyl-hex-5-en-3-one; 5-allyl-5-methyl-hept-6-en-4-one; 5-allyl-5-ethyl-hept-6-en-4-one; 5-allyl-5-propyl-hept-6-en-4-one; 4-methallyl-4-methyl-hex-5-en-3-one; 4-crotyl-4-methyl-hex-5-en-3-one; 4-benzyl-4-methyl-hex-5-en-3-one; 2-allyl-2-vinyl-cyclo-pentanone; 2-allyl-2-vinyl-cyclohexanone; 2-allyl-2-(but-2-enyl)-cyclohexan-1-one; 3-methyl-3-prenyl-pent-4-en-2-one; 3-allyl-3-methyl-octa-4,7-dien-2-one; 3-methyl-3-prenyl-hepta-4,6-dien-2-one; 3-methyl-3-allyl-5-methoxy-pent-4-en-2-one; 3-methoxymethyl-3-prenyl-pent-4-en-2-one.

The preferred process for making the compounds of formula II is characterized by subjecting compounds of formula I

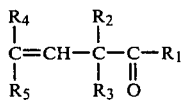

wherein $R_3$ stands for allyl or methallyl, to a temperature treatment of from 80° to 300° C., preferably 150°–220° C.

The reactions can be carried out at atmospheric pressure, thus about 1 bar, in open systems. Sometimes it is, however, advisable to operate in a closed system at 0.5–10 bar. Reaction conditions using a higher pressure and temperature are advisable in order to avoid overlong reaction times, especially when the synthesis of compounds according to the invention is to take place which contain bulky radicals. Also, it is frequently advisable to carry out the reactions in an atmosphere of inert gas, e.g., nitrogen, argon or the like.

The course of the rearrangements can be observed, e.g., by spectroscopic or chromatographic methods, but also by plotting a boiling curve, since the rearranged products practically always have higher boiling points than the starting products.

According to the invention, the starting compounds used are from a variety of compounds of general formula I, in which $R_3$ is the allyl or methallyl radical. These compounds, subjected to the reaction conditions described above, yield rearrangements forming the compounds of formula II. Examples of compounds of formula II are: 3-methyl-3,7-octadien-2-one; 3-ethyl-3,7-octadien-2-one; 3-propyl-3,7-octadien-2-one; 3-butyl-3,7-octadien-2-one; 3-pentyl-3,7-octadien-2-one; 3,7-dimethyl-3,7-octadien-2-one; 3-ethyl-7-methyl-3,7-octadien-2-one; 3-propyl-7-methyl-3,7-octadien-2-one;3-butyl-7-methyl-3,7-octadien-2-one; 3,5-dimethyl-3,7-octadien-2-one; 3,5,5-trimethyl-3,7-octadien-2-one; 3,5,5,7-tetramethyl-3,7-octadien-2-one; 5-ethyl-3,5,7-trimethyl-3,7-octadien-2-one; 3-methyl-5,5-diethyl-3,7-octadien-2-one; 3,5,5-triethyl-3,7-octadien-2-one; 3,5,5-triethyl-7-methyl-3,7-octadien-2-one; 3-propyl-5,5-diethyl-3,7-octadien-2-one; 3-butyl-5,5-dimethyl-3,7-octadien-2-one; 4-methyl-4,8-nonadien-3-one; 4-ethyl-4,8-nonadien-3-one; 4-propyl-4,8-nonadien-3-one; 4,8-dimethyl-4,8-nonadien-3-one; 4-ethyl-8-methyl-4,8-nonadien-3-one; 4-propyl-8-methyl-4,8-nonadien-3-one; 4,6-dimethyl-4,8-nonadien-3-one; 4,6,8-trimethyl-4,8-nonadien-3-one; 4,6,6,8-tetramethyl-4,8-nonadien-3-one; 4,6-diethyl-4,8-nonadien-3-one 4,6,6-triethyl-4,8-nonadien-3-one; 4,6,6-triethyl-8-methyl-4,8-nonadien-3-one; 4,6-dimethyl-6-ethyl-4,8-nonadien-3-one; 4,6-dimethyl-6-propyl-4,8-nonadien-3-one; 4,6,8-trimethyl-6-ethyl-4,8-nonadien-3-one; 2-(2-methyl-pent-4-enyliden)-cyclohexan-1-one; 2-(2-ethyl-pent-4-enyliden)-cyclohexan-1-one; 3-methyl-5-allyl-octa-3,7-dien-2-one; 3-methyl-5-methoxy-octa-3,7-dien-2-one; 3-methoxy-methyl-octa-3,7-dien-2-one.

Furthermore, the invention relates to compounds which are formed by addition of hydrogen to at least one carbonyl or olefin double bond of compounds of formula I and II. The addition of hydrogen to at least one double bond of the mentioned compounds of the invention may be brought about in a manner known per se.

Examples of hydrogenating agents which selectively hydrogenate the carbonyl group are sodium boranate, lithium alanate, and others. Total hydrogenation may be carried out, e.g., with molecular hydrogen and Raney nickel. If desired, selective hydrogenation can be brought about on unprotected carbon double bonds with molecular hydrogen in the presence of less active catalysts of the platinum metals, while carbon double bonds protected by substituents remain unchanged.

Examples of modified compounds formed by hydrogen addition from compounds of formulas I and II are, for instance: 3-allyl-3-methyl-pent-4-en-2-ol; 3-allyl-3-ethyl-pent-4-en-2-ol; 3-allyl-3-propyl-pent-4-en-2-ol; 3-ethyl-3-methyl-hexan-2-ol; 3-ethyl-3,3-diethyl-hexan-2-ol; 3-methyl-3-propyl-hexan-2-ol; 3-methallyl-3-methyl-pent-4-en-2-ol; 3-ethyl-3,5-dimethyl-hexan-2-ol; 3,3-diethyl-3-methyl-hexan-2-ol; 3-ethyl-3-methyl-3-propyl-hexan-2-ol; 3-crotyl-3-methyl-pent-4-en-2-ol; 3-crotyl-3-ethyl-pent-4-en-2-ol; 3-benzyl-3-methyl-pent-4-en-2-ol; 3-ethyl-3-methyl-heptan-2-ol; 3,3-diethyl-heptan-2-ol; 3-benzyl-3-methyl-pent-4-en-2-ol; 3-benzyl-3-methyl-pentan-2-ol; 3-benzyl-3-ethyl-pentan-2-ol; 3-allyl-3-methyl-hex-4-en-2-ol; 3-allyl-3-ethyl-hex-4-en-2-ol; 3-allyl-3-propyl-hex-4-en-2-ol; 3-methyl-3-propyl-hexan- 2-ol; 3-ethyl-3-propyl-hexan-2-ol; 3,3-dipropyl-3-hexan-2-ol; 3-methyl-3-methallyl-hex-4-en-2-ol; 3-ethyl-3-methallyl-hex-4-en-2-ol; 3,5-dimethyl-3-propyl-hexan-2-ol; 3-ethyl-3-propyl-5-methyl-hexan-2-ol; 3-benzyl-3-methyl-hex-4-en-2-ol; 3-benzyl-3-methyl-hexan-2-ol; 3-allyl-3-methyl-hept-4-en-2-ol; 3-allyl-3-ethyl-hept-4-en-2-ol; 3-methyl-3-propyl-heptan-2-ol; 3-ethyl-3-propyl-heptan-2-ol; 3,3-dipropyl-3-heptan-2-ol; 4-methyl-4-vinyl-hept-6-en-3-ol; 4-ethyl-4-methyl-heptan-3-ol; 5-methyl-5-vinyl-oct-7-en-4-ol; 5-ethyl-5-methyl-octan-4-ol; 5-ethyl-5-vinyl-oct-7-en-4-ol; 5,5-diethyl-octan-4-ol; 5-propyl-5-vinyl-oct-7-en-4-ol; 5-ethyl-5-propyl-octan-4-ol; 4,6-dimethyl-4-vinyl-hept-6-en-3-ol; 4-ethyl-4,6-dimethyl-heptan-3-ol; 4-methyl-4-vinyl-oct-3-ol; 4-ethyl-4-methyl-octan-3-ol; 2-allyl-2-vinyl-cyclopentan-1-ol; 2-ethyl-2-propyl-cyclopentan-1-ol; 2-allyl-2-vinyl-cyclohexan-1-ol; 2-ethyl-2-propyl-cyclohexan-1-ol; 3-methyl-3-prenyl-pent-4-en-2-ol; 3-allyl-3-methyl-octa-4,7-dien-2-ol; 3-methyl-3-prenyl-hepta-4,6-dien-2-ol; 3-methyl-3-propyl-5-methoxy-pentan-2-ol; 3-methoxymethyl-3-prenyl-pent-4-en-2-ol; 3-p-methoxybenzyl-b 3-methyl-pentan-2-ol; 3-methyl-3-propyl-octan-2-ol; 3-methyl-3,7-octadien-2-ol; 3-ethyl-3,7-octadien-2-ol; 3-propyl-3,7-octadien-2-ol; 3,5-dimethyl-3,7-octadien-2-ol; 3,7-dimethyl-3,7-octadien-2-ol; 3,5,5-trimethyl-3,7-octadien-2-ol; 3,5,5,7-tetramethyl-3,7-octadien-2-ol; 3-ethyl-7-methyl-3,7-octadien-2-ol; 3-propyl-7-methyl-3,7-octadien-2-ol; 3-methyl-5,5-dimethyl-3,7-octadien-2-ol; 3,5,5-trimethyl-octan-2-ol; 3,5,5,7-tetramethyl-octan-2-ol; 3-methyl-5,5-diethyl-octan-2-ol; 4-methyl-4,8-nonadien-3-ol; 4-ethyl-4,8-nonadien-3-ol; 4,8-dimethyl-4,8-nonadien-3-ol; 4-propyl-8methyl-4,8- nonadien-3-ol; 4,6,8-trimethyl-4,8-nonadien-3-ol; 4,6-dimethyl-nonan-3-ol; 4,6,6-triethyl-nonan-3-ol; 4,6,8-trimethyl-nonan-3-ol; 3-methyl-5-allyl-octa-3,7-dien-2-ol; 3-methyl-5-propyl-octan-2-ol; 3-methyl-5-methoxy-octa-3,7-dien-2-ol; 3-methoxymethyl-octa-3,7-dien-2-ol; 2-(2-ethyl-pent-4-enyliden)-cyclohexan-1-ol; 2-(2-ethyl-pentyl)-cyclohexan-1-ol.

The compounds according to the invention are used as fragrances and flavoring agents. It is possible, e.g., to obtain fruity, woody, or herbal aromas and flavoring nuances. They are also useful as intermediates for pesticides and pharmaceuticals. Finally, such monomer compounds according to the invention which contain multiple bonds, are useful for the preparation of valuable polymers or condensates.

With the process according to the invention, it is possible to selectively produce new unsaturated ketones having a double carbon bond in $\beta$-$\gamma$-position with respect to the carbonyl functional group. In general, it is possible to use basic chemicals industrially available, in large amounts. Finally, the ketones having allyl substituents can be converted to isoprenoid systems.

In the following, the invention will be more fully described in a number of examples, but it should be understood that these are given by way of illustration and not of limitation.

EXAMPLE 1

3-Benzyl-3-methyl-pent-4-en-2-one

Into a one liter four-neck flask equipped with stirrer, thermometer, dropping funnel and reflux cooler, 160 g 50% NaOH, 50 ml water, 200 ml toluene and 10 g tetrabutyl ammonium iodide are first introduced and heated to 60° C. Then, a mixture of 98 g (one mole) 3-methyl-pent-3-en-2-one and 158 g (1.25 mole) benzyl chloride are added dropwise while stirring vigorously at a rapid rate which allows a temperature of 65° to 70° C. to be maintained (time: about 1 hour). Thereafter, the mixture is refluxed for one more hour.

For further processing, 100 ml water are added, the phases are separated and the organic phase, after withdrawal of the solvent, is fractionally distilled over a 30 cm Vigreux column.

Obtained are 130 g of the desired product (69% of the theoretical amount calculated on the ketone used).

Fraction B.p.$_{0.01}$ 85° to 87° C., colorless oil.
Odor: sweet, woody.

EXAMPLE 2

3-Methyl-3-prenyl-pent-4-en-2one

In a manner similar to Example 1, 100 ml toluene, 100 ml 50% NaOH, and 10 g tetrabutyl ammonium iodide are introduced into a 500 ml flask, and heated to 60° C.

Without further heating, and while stirring, 52.3 g (0.5 moles) prenyl chloride are added in mixture with 49 g (0.5 moles) 3-methyl-pent-3-en-2-one within 1.5 hours. The reaction mixture is further maintained at 60°–70° C. for 3 hours. For better phase separation, the mixture is diluted with 100 ml water, the aqueous phase is extracted once with 50 ml toluene, and the combined organic phases, after withdrawing of the solvent, is fractionally distilled.

The yield is 46 g of the desired product (55% of the theoretical amount).

Fraction B.p.$_{12}$ 84°–85° C., colorless liquid.
Odor: Licorice-like.

EXAMPLE 3

3-Allyl-3-methyl-pent-4-en-2one

Under the conditions described in Example 2, 49 g (0.5 moles) 3-methyl-pent-3-en-2-one are reacted with 51 ml (0.625 moles) allyl chloride.

Further work-up by phase separation and fractional distillation yields 24 g of the desired product (35% of the theoretical amount).

Fraction B.p.$_{12}$ 64°–65° C., colorless liquid.
Odor: Peppermint-terpene-like.

EXAMPLE 4

3-Methyl-octa-3,7-dien-2-one 100 g 3-allyl-3-methyl-pent-4-en-2-one are refluxed in a 250 ml flask equipped with reflux cooler, while gaseous nitrogen is passed through. Within 19 hours, the temperature in the flask rises from 165° to 180° C. The GC-spectrum then shows a complete rearrangement.

The subsequent distillation yeilds 92.8 g of the desired product (92.8% of the theoretical amount).

B.p.$_{12}$ 79°–80° C., colorless liquid.

EXAMPLE 5

3-Allyl-3-methyl-octa-4,7-dien-2one

Following the same procedure as in Example 1, a mixture of 138 g (1 mole) of 3-methyl-octa-3,7-dien-2one and 92 g (1.2 moles) allyl chloride are added in doses at 60° C. while stirring. The reaction mixture is maintained 3 more hours at 70° C., then separated into phases, with the organic phase being dried with sodium sulfate and then fractionally distilled over a 30 cm Vigreux column.

The yield is 110.5 g (62% of the theoretical value calculated on the ketone used).

Fraction Bp$_{12}$ 103° C., colorless oil.
Odor: Peppery-fruity.

EXAMPLE 6

3-Methyl-5-allyl-octa-3,7-dien-2-one

In the apparatus used in Example 4, 100 g 3-allyl-3-methyl-4,7-octadien-2-one are heated for 30 hours to 185°–190° C. Subsequently, the reaction mixture is fractionally distilled.

The yield of desired product is 83.4 g (83.4% of the theoretical amount).

Fraction Bp$_{12}$ 107°–108° C., colorless oil.
Odor: Fruity.

EXAMPLE 7

3-Benzyl-3-methyl-pent-4-en-2-ol

Into a 250 ml two-neck flask with dropping funnel and reflux cooler, 1.1 g (0.029 moles) LiAlH$_4$ in 100 ml absolute ether is fist introduced. While stirring, a solution of 18.8 g (0.1 mole) 3-benzyl-3-methyl-pent-4-en-2-one (according to Example 1) is dissolved in 40 ml absolute ether, so rapidly that the mixture keeps boiling at a moderate level. The reaction mixture is maintained on reflux for one more hour, then hydrolyzed with ice water weakly acidified with 2 n-H$_2$SO$_4$. The phases are separaated and the organic phase, after drying with sodium sulfate, is subjected to vacuum distillation.

The yield in desired product is 14.9 g (78.4% of the theoretical amount).

Bp$_{0.01}$ 88° C., colorless oil.

EXAMPLE 8

3-Allyl-3-methyl-pent-4-en-2-ol

In an analogous manner to that of Example 7, 27.6 g (0.2 moles) 3-allyl-3-methyl-pent-4-en-2-one (according to Example 3) are reduced with 2.2 g (0.058 moles) LiAlH$_4$.

The yield was 24 g, corresponding to 85.7% of the theoretical amount.

Bp$_{12}$ 67°–69° C., colorless oil.

EXAMPLE 9

3-Methyl-5-allyl-octa-3,7-dien-2-ol

In an analogous manner to that of Example 7, 17.8 g (0.1 moles) 3-methyl-5-allyl-octa-3,7-dien-2-one (according to Example 6) are reacted with 1.1 g (0.029 moles) LiAlH$_4$.

The yield is 15.2 g (84.4% of the theoretical amount).
Bp$_{12}$ 115° C., colorless oil.
Odor: Pine-like.

Thus, while only several examples of the present invention have been shown and described, it will be obvious that many changes and modifications may be made thereunto, without departing from the spirit and scope of the invention.

What is claimed is:

1. A compound of the general formula I

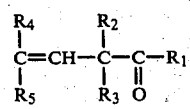

wherein:
R$_1$ is a member selected from the group consisting of an alkyl radical with 1–6 carbon atoms, an alkoxyalkyl radical with 1–6 carbon atoms, and a phenyl radical containing up to two substituents, said substituents being selected from the group consisting of up to two alkyl radicals having from 1–3 carbon atoms, up to two alkoxyalkyl radicals having from 1–3 carbon atoms, and up to two halogen atoms;
R$_2$ is a member selected from the group consisting of an alkyl radical with 1–5 carbon atoms, an alkoxyalkyl radical with 1–5 carbon atoms, and a phenyl radical with up to two substituents, said substituents being selected from the group consisting of up to two alkyl radicals having from 1–3 carbon atoms, up to two alkoxyalkyl radicals having from 1–3 carbon atoms, and up to two halogen atoms, or R$_1$ and R$_2$ together form a ring radical with 4–7 carbon atoms;
R$_3$ is a member selected from the group consisting of an allylic radical having 3–5 carbon atoms, and a benzylic radical having up to two substituents on the aromatic ring, said substituents being selected from the group consisting of up to two alkyl radicals with 1–3 carbon atoms, up to two alkoxyalkyl radicals having 1–3 carbon atoms and up to two halogen atoms; and
R$_4$ and R$_5$ each represent a member selected from the group consisting of an alkyl radical with 1–6 carbon atoms, an alkoxyalkyl radical with 1–6 carbon atoms, an alkenyl radical with 2–6 carbon atoms, and a phenyl radical with up to two substituents, said substituents being selected from the group consisting of up to two alkyl radicals with 1–3 carbon atoms, up to two alkoxyalkyl radicals with 1–3 carbon atoms, and up to two halogen atoms.

2. The compound according to claim 1 wherein R$_1$ and R$_2$ together form a ring radical with 4–7 carbon atoms.

3. The compound according to claim 1, wherein R$_3$ is a member selected from the group consisting of an allyl radical and a methallyl radical.

4. A compound of the general formula II

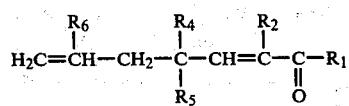

wherein:
R$_1$ represents a member selected from the group consisting of an alkyl radical having 1–6 carbon atoms, an alkoxyalkyl radical having 1–6 carbon atoms, and a phenyl radical containing up to two substituents, said substituents being selected from the group consiting of up to two alkyl radicals with 1–3 carbon atoms, up to two alkoxyalkyl radicals with 1–3 carbon atoms, and up to two halogen atoms;
R$_2$ is a member selected from the group consisting of an alkyl radical with 1–5 carbon atoms, an alkoxyalkyl radical with 1–5 carbon atoms, and a phenyl radical having a maximum of two substituents, said substituents being selected from the group consisting of up to two alkyl radicals having from 1–3 carbon atoms, up to two alkoxyalkyl radicals having from 1–3 carbon atoms, and up to two halogen atoms, or R$_1$ and R$_2$ together form a ring radical with 4–7 carbon atoms;
R$_4$ and R$_5$ each represent a member selected from the group consisting of hydrogen, an alkyl radical with 1–6 carbon atoms, an alkoxyalkyl radical with 1–6 carbon atoms, an alkenyl radical with 2–6 carbon atoms, and a phenyl radical containing up to two substituents, said substituents being selected from the group consisting of up to two alkyl radicals with 1–3 carbon atoms, up to two alkoxyalkyl radicals with 1–3 carbon atoms, and up to two halogen atoms; and
R$_6$ represents hydrogen or methyl.

5. The compound according to claim 4, wherein R$_1$ and R$_2$ together form a ring radical with 4–7 carbon atoms.

6. A compound of the general formula III

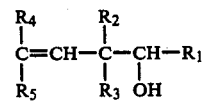

wherein:
R$_1$ is a member selected from the group consisting of an alkyl radical with 1–6 carbon atoms, an alkoxyalkyl radical with 1–6 carbon atoms, and a phenyl radical containing up to two substituents, said substituents being selected from the group consisting of up to two alkyl radicals having from 1–3 carbon atoms, up to two alkoxyalkyl radicals having from 1–3 carbon atoms, and up to two halogen atoms;
R$_2$ is a member selected from the group consisting of an alkyl radical with 1–5 carbon atoms, an alkoxyalkyl radical with 1-5 carbon atoms, and a phenyl radical with up to two substituents, said substituents being selected from the group consisting of up to two alkyl radicals having from 1-3 carbon atoms, up to two alkoxyalkyl radicals having from 1-3 carbon atoms, and up to two halogen atoms, or $R_1$ and $R_2$ together form a ring radical with 4-7 carbon atoms;

$R_3$ is a member selected from the group consisting of an allylic radical having 3-5 carbon atoms, and a benzylic radical having up to two substituents on the aromatic ring, said substituents being selected from the group consisting of up to two alkyl radicals with 1-3 carbon atoms, up to two alkoxyalkyl radicals having 1-3 carbon atoms and up to two halogen atoms; and $R_4$ and $R_5$ each represent a member selected from the group consisting of hydrogen, an alkyl radical with 1-6 carbon atoms, an alkoxyalkyl radical with 1-6 carbon atoms, an alkenyl radical with 2-6 carbon atoms, and a phenyl radical containing up to two substituents, said substituents being selected from the group consisting of up to two alkyl radicals with 1-3 carbon atoms, up to two alkoxyalkyl radicals with 1-3 carbon atoms, and up to two halogen atoms.

7. The compound according to claim 6, wherein $R_1$ and $R_2$ together form a ring radical with 4-7 carbon atoms.

8. The compound according to claim 6, wherein $R_3$ is a member selected from the group consisting of an allyl radical and a methallyl radical.

9. A compound of the general formula IV

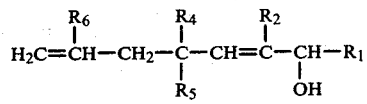

wherein:

$R_1$ represents a member selected from the group consisting of an alkyl radical having 1-6 carbon atoms, an alkoxyalkyl radical having 1-6 carbon atoms, and a phenyl radical containing up to two substituents, said substituents being selected from the group consiting of up to two alkyl radicals with 1-3 carbon atoms, up to two alkoxyalkyl radicals with 1-3 carbon atoms, and up to two halogen atoms;

$R_2$ is a member selected from the group consisting of an alkyl radical with 1-5 carbon atoms, an alkoxyalkyl radical with 1-5 carbon atoms, and a phenyl radical having a maximum of two substituents, said substituents being selected from the group consisting of up to two alkyl radicals having from 1-3 carbon atoms, up to two alkoxyalkyl radicals having from 1-3 carbon atoms, and up to two halogen atoms, or $R_1$ and $R_2$ together form a ring radical with 4-7 carbon atoms;

$R_4$ and $R_5$ each represent a member selected from the group consisting of hydrogen, an alkyl radical with 1-6 carbon atoms, an alkoxyalkyl radical with 1-6 carbon atoms, an alkenyl radical with 2-6 carbon atoms, and a phenyl radical containing up to two substituents, said substituents being selected from the group consisting of up to two alkyl radicals with 1-3 carbon atoms, up to two alkoxyalkyl radicals with 1-3 carbon atoms, and up to two halogen atoms; and $R_6$ represents hydrogen or methyl, 10. The compound according to claim 9, wherein $R_1$ and $R_2$ together form a ring radical with 4-7 carbon atoms.

* * * * *